US007118713B2

United States Patent
Brock et al.

(10) Patent No.: US 7,118,713 B2
(45) Date of Patent: Oct. 10, 2006

(54) TRAY ASSEMBLY FOR OPTICAL INSPECTION APPARATUS

(75) Inventors: David A. Brock, Elkhart, IN (US);
Donald R. Hesser, Elkhart, IN (US);
Gary H. Krauth, Hopedale, MA (US);
Jack L. Zuidema, Elkhart, IN (US);
David L. Boger, St. Louis, MO (US);
Kevin J. Sheldrake, Sudbury (GB)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

(21) Appl. No.: 10/821,441

(22) Filed: Apr. 9, 2004

(65) Prior Publication Data

US 2004/0247491 A1 Dec. 9, 2004

Related U.S. Application Data

(60) Provisional application No. 60/475,288, filed on Jun. 3, 2003.

(51) Int. Cl.
*B01L 9/00* (2006.01)

(52) U.S. Cl. ........................ 422/104; 422/99

(58) Field of Classification Search .............. 422/99, 422/104, 102, 82.05, 68.1, 62.05
See application file for complete search history.

(56) References Cited

U.S. PATENT DOCUMENTS

| 3,998,145 A | * | 12/1976 | Maisch ...................... 99/339 |
| 5,654,803 A | | 8/1997 | Howard, III et al. ....... 356/446 |
| 5,945,341 A | | 8/1999 | Howard, III ................. 436/46 |
| 6,239,445 B1 | * | 5/2001 | Shaeef ....................... 250/576 |
| 2002/0015667 A1 | * | 2/2002 | Chow ........................ 422/100 |

* cited by examiner

*Primary Examiner*—Jill Warden
*Assistant Examiner*—Natalia Levkovich
(74) *Attorney, Agent, or Firm*—McDermott Will & Emery LLP (57) ABSTRACT

A tray assembly for use with an apparatus adapted to inspect a liquid sample, including a support tray insertable within an inspection location within the liquid sample inspection apparatus so that a light source of the apparatus illuminates a liquid sample carried on the support tray and a detector of the apparatus receives light from the liquid sample when the support tray is positioned at the inspection location, and an insert supported within the support tray and having a first surface adapted to receive a first type of liquid carrier and a second surface adapted to receive a second type of liquid carrier different from the first type of liquid carrier.

26 Claims, 10 Drawing Sheets

TRAY ASSEMBLY FOR OPTICAL INSPECTION APPARATUS

CROSS-REFERENCE TO RELATED APPLICATIONS

The present application claims priority from co-pending provisional U.S. patent application Ser. No. 60/475,288, filed Jun. 3, 2003, which is incorporated herein by reference in its entirety.

FIELD OF THE INVENTION

The present disclosure relates to an apparatus and method for performing tests on a sample of body fluid to be optically inspected and, more particularly, to a liquid sample carrier tray for use with the apparatus. Even more particularly, the present disclosure relates to a tray assembly for alternatively supporting at least two different types of liquid sample carriers for testing within an optical inspection apparatus.

BACKGROUND OF THE DISCLOSURE

It is useful for various medical diagnostic purposes to utilize a reflectance spectroscope to analyze samples of body fluid, for example, to determine the color of a person's urine. A conventional spectroscope may determine the color of a urine sample disposed on a white, non-reactive pad by illuminating the pad and taking a number of reflectance readings from the pad, each having a magnitude relating to a different wavelength of visible light. The color of the urine on the pad may then be determined based upon the relative magnitudes of red, green, blue and infrared reflectance signals.

Conventional spectroscopes may be used to perform a number of different urinalysis tests utilizing a reagent strip on which a number of different reagent pads are disposed. Each reagent pad may be provided with a different reagent which causes a color change in response to the presence of a certain type of constituent in urine, such as leukocytes (white blood cells) or red blood cells. Such a reagent strip may have ten or more different types of reagent pads.

In a conventional spectroscope, the process of inspecting a reagent strip may be performed by dipping the reagent strip in a urine sample, blotting excess urine from the reagent strip, placing the reagent strip at a designated location in the spectrophotometer, and pressing a start button which causes the spectroscope to begin automatic processing and inspection of the reagent strip.

For example, U.S. Pat. No. 5,654,803, which is assigned to the assignee of the present disclosure, discloses an apparatus and method for determination of non-hemolyzed levels of occult blood in urine. The apparatus is provided with a light bulb for successively illuminating a plurality of different portions of a reagent pad on which a urine sample is disposed, and a detector array for detecting light received from the reagent pad and generating a plurality of reflectance signals in response to light received from a corresponding one of the different portions of the reagent pad. The apparatus is also provided with means for determining whether the magnitude of one of the reflectance signals is substantially different from the magnitude of another of the reflectance signals. Where the body-fluid sample is urine, this capability allows the apparatus to detect the presence of non-hemolyzed levels of occult blood in the urine sample. The light bulb may successively illuminate a plurality of overlapping portions of the reagent pad, and may successively illuminate at least tree different portions of the reagent pad which are linearly offset from each other.

U.S. Pat. No. 5,945,341, which is also assigned to the assignee of the present disclosure, discloses a system for the optical identification of coding on a diagnostic test strip and an automated method for reading a test strip for the analysis of the presence of one or more analytes in a liquid test sample. The method involves the spectrophotometric reading of a test strip which bears at least two marker fields on its surface which are capable of reflecting light at different spectral regions from each other. The means of the spectrophotometer is programmed to discern information concerning the strip, such as what analyte the strip is designed to detect, from the sequences of spectral classifications by spectral reflectance measurements of the strip's marker fields.

U.S. Pat. No. 6,239,445, which is assigned to the assignee of the present disclosure, discloses an optical inspection apparatus for inspecting a liquid sample, such as urine. The apparatus includes a tray that is adapted to be physically coupled to a first liquid sample carrier and a second liquid sample carrier, which are both adapted to hold a liquid sample. The first liquid sample carrier is of a first type, such as a reagent cassette, and the second liquid sample carrier is of a second type, such as a reagent strip, different from the first type. The apparatus has a light source adapted to illuminate one of the liquid samples associated with one of the liquid sample carriers when the liquid sample carrier is coupled to the tray at an inspection location and a detector adapted to receive light from the liquid sample when the liquid sample is being illuminated by the light source.

What is still desired is a new and improved tray assembly including a support tray that is adapted to be physically coupled to at least two different liquid sample carriers such as a reagent cassette and a reagent strip. Preferably, the new and improved tray assembly will be user-friendly and easy to use. In addition, the new and improved tray assembly will preferably be easy to clean and less likely to contaminate the optical inspection apparatus with excess bodily fluids from the liquid sample carriers.

SUMMARY OF THE DISCLOSURE

The disclosure is directed to exemplary embodiments of a new and improved tray assembly which allows different types of liquid carriers to be utilized in an liquid sample inspection apparatus in a simple and convenient manner. The new and improved tray assembly is user-friendly and easy to use.

One exemplary embodiment of the tray assembly includes a support tray insertable within an inspection location within the liquid sample inspection apparatus so that a light source of the apparatus illuminates a liquid sample carried on the support tray and a detector of the apparatus receives light from the liquid sample when the support tray is positioned at the inspection location, and an insert supported within the support tray and having a first surface adapted to receive a first type of liquid carrier and a second surface adapted to receive a second type of liquid carrier different from the first type of liquid carrier.

According to one aspect of the present disclosure, the first type of liquid carrier comprises a reagent cassette, and the first surface of the insert has a recess shaped to receive a first portion of the reagent cassette. According to another aspect, the second type of liquid carrier comprises a reagent strip having a plurality of reagent pads disposed thereon, and the second surface of the insert has an elongated channel sized to accommodate the reagent strip.

Another exemplary embodiment of the tray assembly of the present disclosure includes a support tray insertable within an inspection location within the liquid sample inspection apparatus. The support tray includes first and second opposing ends, and a top surface extending between the first and second opposing ends and having a compartment. The compartment has an open end at the first end of the support tray and an end wall nearer the second end of the support tray. The assembly also includes an insert movably supported within the compartment of the support tray and movable between a first position adjacent the end wall of the compartment and a second position adjacent the open end of the compartment. When the insert is in the first position the compartment is adapted to receive a first type of liquid carrier adjacent the open end of the compartment. The insert includes a surface adapted to receive a second type of liquid carrier different from the first type of liquid carrier. The assembly is adapted to support the second type of liquid carrier when the insert is in the second position.

Additional aspects and advantages of the present disclosure will become readily apparent to those skilled in this art from the following detailed description, wherein only exemplary embodiments of the present disclosure are shown and described, simply by way of illustration of the best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

Reference is made to the attached drawings, wherein elements having the same reference character designations represent like elements throughout, and wherein.

DETAILED DESCRIPTION OF EXEMPLARY EMBODIMENTS

Figure 1:
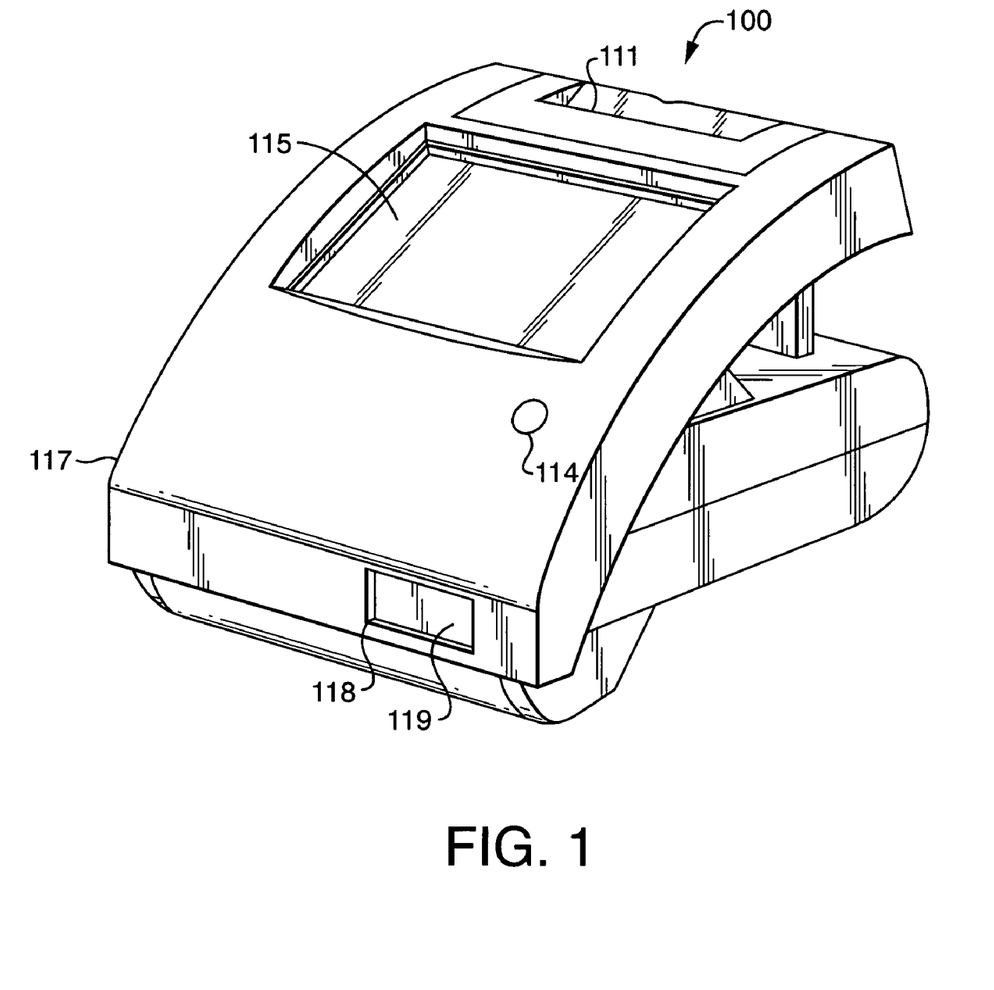
FIG. 1 is a perspective view of an optical inspection apparatus constructed in accordance with the present disclosure, which may be used to perform various tests of a body fluid sample.

FIGS. 2 through 6 show an exemplary embodiment of a new and improved tray assembly 200 constructed in accordance with the present disclosure for use with the apparatus 100 of FIG. 1. The apparatus 100 of FIG. 1 is a reflectance spectroscope, for optically inspecting liquid samples such as body fluid samples, placed on a liquid carrier, such as a reagent cassette 122 or a reagent strip 146. The tray assembly 200 includes a support tray 202 and an insert 204 that fits into the support tray with one of a first surface 206, adapted to hold the reagent cassette 122, and a second surface 208, adapted to hold the reagent strip 146, facing upwardly so that one of the reagent cassette 122 and the reagent strip 146 can be held by the insert 204 in the support tray 202.

Figure 11:
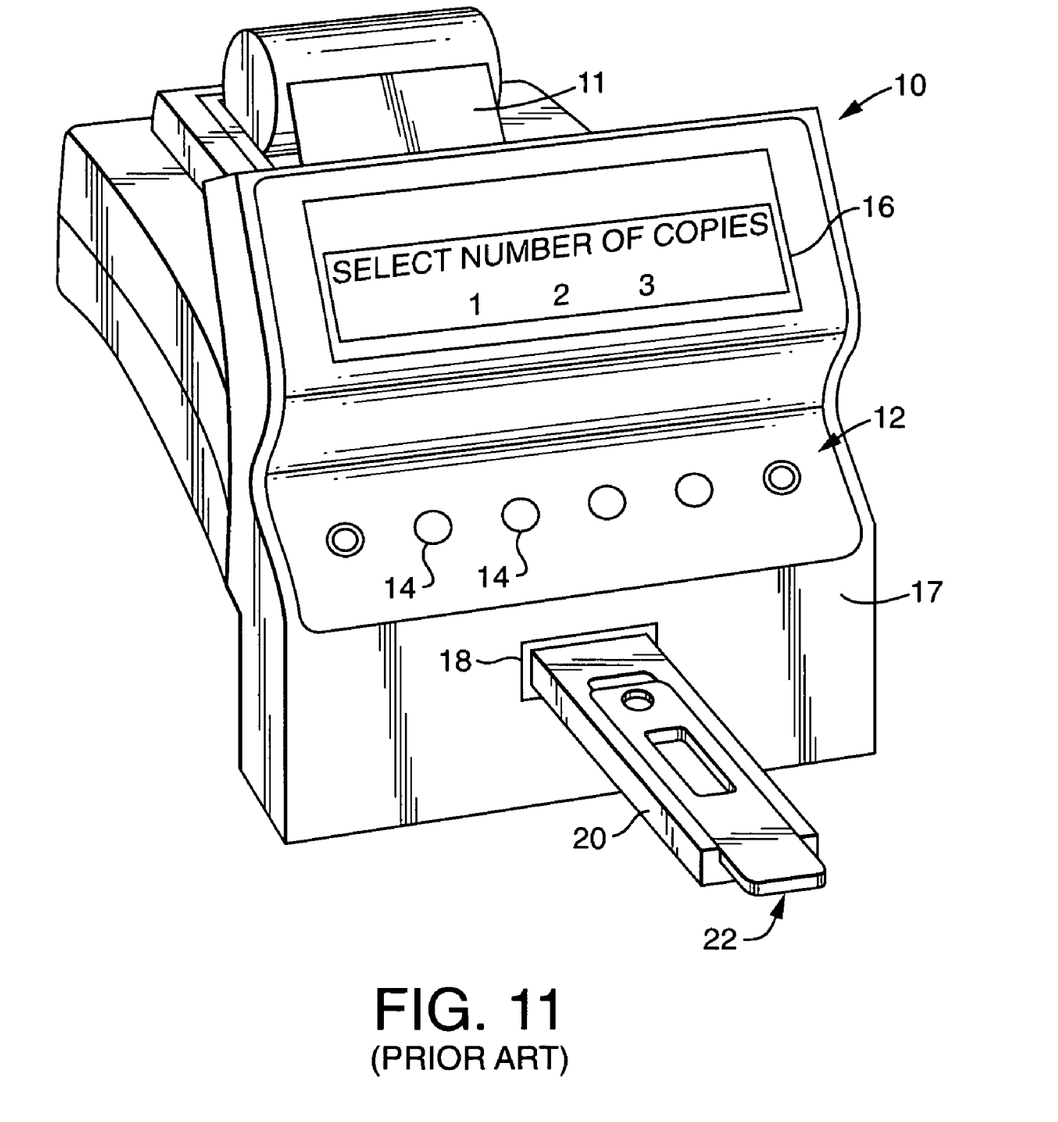
FIG. 11 is a perspective view of an optical inspection apparatus constructed in accordance with the prior art, which may be used to perform various tests of a body fluid sample.

Prior to discussing the new and improved tray assembly 200 of FIGS. 2 through 6, however, the prior art shown in FIGS. 11 through 14 will first be discussed to provide background information. FIG. 11 illustrates an inspection apparatus 10, such as a reflectance spectroscope, for optically inspecting liquid samples such as body fluid samples. The apparatus 10 includes a support tray, which is also shown in FIGS. 18 and 19. The particular apparatus 10 shown in FIG. 11 is a CLINITEK® 50 Urine Chemistry Analyzer available from Bayer Corporation, Diagnostics Division, of Tarrytown, N.Y. The apparatus 10 is described in greater detail in U.S. Pat. Nos. 5,654,803; 5,945,341; and 6,239,445, which are assigned to the assignee of the present disclosure and incorporated herein by reference.

Figure 12:
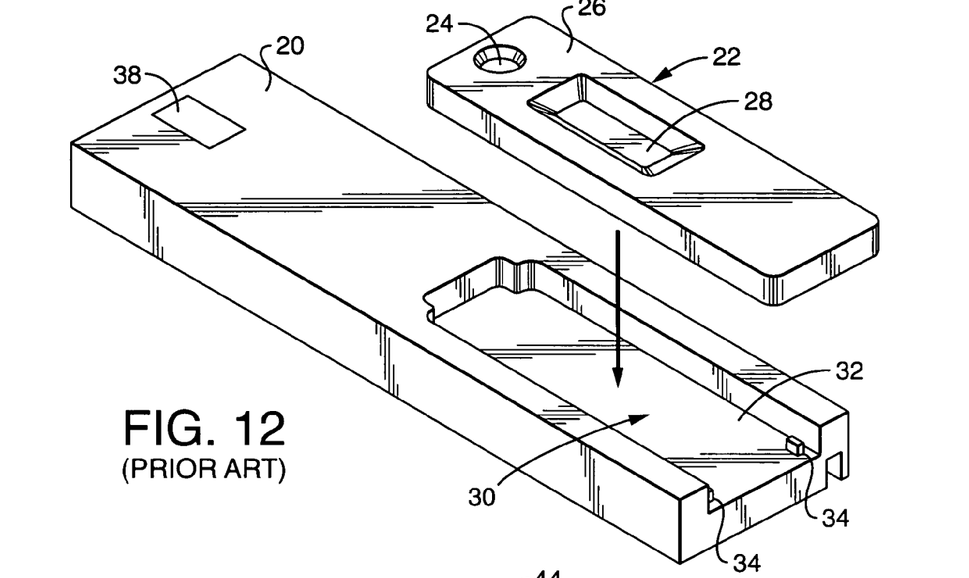
FIG. 12 is a perspective view of a support tray, constructed in accordance with the prior art, of the apparatus of FIG. 11, and a reagent cassette that may be inserted into the support tray.

The inspection apparatus 10 has an integral keyboard 12 for user input, and a visual display 16 for displaying various messages to a user relating to the operation of the inspection apparatus 10. The inspection apparatus 10 also has a housing 17 with an opening 18 formed therein into which the support tray 20 may be retracted. As shown in FIGS. 11 and 12, the support tray 20 is adapted to receive a first type of liquid carrier or removable insert, which may be in the form of a reagent cassette 22.

The reagent cassette 22 may be a disposable, single-use cassette for doing a pregnancy test, for example, in a conventional manner. The reagent cassette 22 has an opening or well 24 formed in an upper surface 26 into which a body fluid sample, such as urine, is placed. The interior of the reagent cassette 22 has a reagent strip (not shown) which may react with the body fluid sample placed in the well 24. Depending on the results of the test, the reagent strip may change color (e.g., a colored stripe may appear), which is determinable from viewing the reagent strip through a window 28 formed in the upper surface 26 of the reagent cassette 22.

As shown in FIG. 12, the support tray 20 has a rectangular recess 30 sized so that the reagent cassette 22 may be placed therein. As shown in FIGS. 11 and 12, the reagent cassette 22 is longer than the recess 30 so that when the reagent cassette 22 is placed within the recess 30, a portion of the reagent cassette 22 extends outwardly beyond the end of the support tray 20 in order to enable a user to grasp the outwardly extending end of the reagent cassette 22 and lift it out of the recess 30.

Referring to FIG. 12, an upper surface 32 of the recess 30 has a plurality of upwardly extending locating members 34, which may be in the form of pins, for example. When the reagent cassette 22 is placed within the support tray 20, the locating members 34 are positioned within a plurality of apertures or holes (not shown) formed in the bottom surface of the reagent cassette 22, so that the locating members 34 prevent the reagent cassette 22 from inadvertently sliding out of the recess 30. The support tray 20 may have a conventional calibration chip 38 of a certain color, such as white, disposed in its upper surface to facilitate calibration in a conventional manner.

Figure 13:
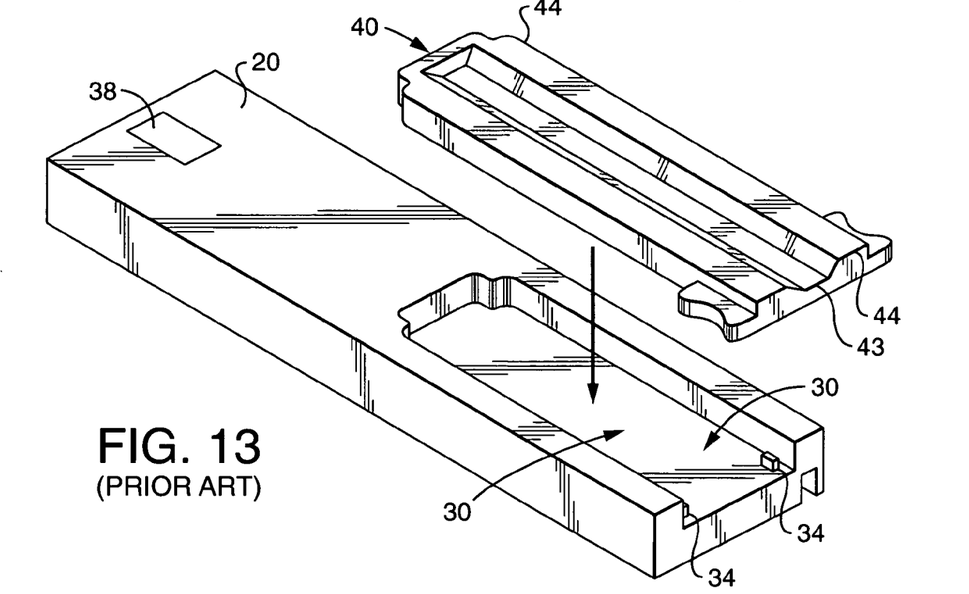
FIG. 13 is a perspective view of the support tray of the apparatus of FIG. 11 and a reagent strip holder, constructed in accordance with the prior art, that may be inserted into the support tray.

Referring to FIG. 13, the support tray 20 is also adapted to receive a second type of liquid carrier or removable insert, which may be in the form of a reagent strip holder 40. The outer dimensions of the reagent strip holder 40 are generally the same as the outer dimensions of the reagent cassette 22 so that the reagent strip holder 40 also fits within the recess 30. The reagent strip holder 40 has a plurality of apertures or holes (not shown) formed in its bottom surface which are positioned to receive the locating members 34 to prevent the reagent strip holder 40 from inadvertently sliding out of the recess 30, as described above in connection with the reagent cassette 22.

As shown in FIG. 13, the reagent strip holder 40 is longer than the recess 30 so that when the reagent strip holder 40 is placed within the recess 30, a portion of the reagent strip holder 40 extends outwardly beyond the end of the support tray 20 in order to enable a user to grasp the outwardly extending end of the reagent strip holder 40 and lift it out of the recess 30.

Figure 14:
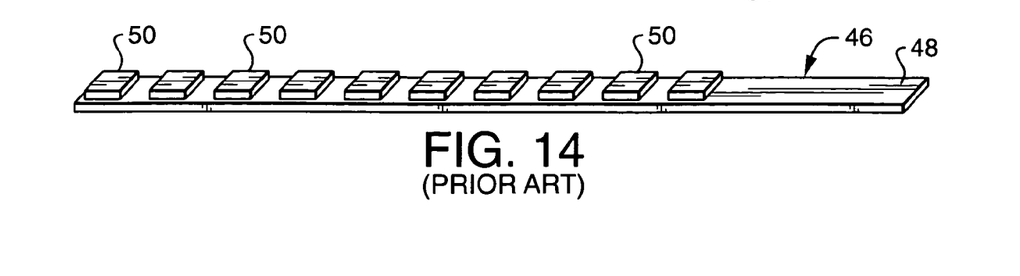
FIG. 14 is a perspective view of a reagent strip, constructed in accordance with the prior art, usable with the reagent strip holder of FIG. 13.

The reagent strip holder 40 has a central channel 43 formed therein which is sized to conform to the shape of a reagent strip 46, an example of which is shown in FIG. 14. The reagent strip holder 40 may have a raised lip 44 which is disposed around the periphery of the reagent strip holder 40 to reduce the likelihood of body fluid samples contaminating the support tray 20.

Referring to FIG. 14, the reagent strip 46 may have a thin, non-reactive substrate 48 on which a number of reagent pads 50 are fixed. Each reagent pad 50 may be composed of a relatively absorbent material impregnated with a respective reagent, each reagent and reagent pad 50 being associated with a particular test to be performed. When urinalysis tests are performed, they may include, for example, a test for leukocytes in the urine, a test of the pH of the urine, a test for blood in the urine, etc. When each reagent pad 50 comes into contact with a urine sample, the pad changes color over a time period, depending on the reagent used and the characteristics of the urine sample. The reagent strip 46 may be, for example, a MULTISTIX® reagent strip commercially available from Bayer Corporation, Diagnostics Division, of Tarrytown, N.Y.

Referring back to FIG. 11, during an inspection procedure the support tray 20 is moved between an outwardly extended position as shown in FIG. 11 and an optical inspection position in which the tray 20 is retracted inwardly into the housing 17 of the inspection apparatus 10. The inspection apparatus 10 may be used to optically inspect multiple reagent cassettes 22 and multiple reagent strips 46 in any order desired by the user, since the reagent cassettes 22 and the reagent strip holder 40 have the same outer dimensions and fit within the recess 30 in the support tray 20.

In using the inspection apparatus 10, the user may prepare a reagent cassette 22 for optical inspection by putting a body fluid sample in the well 24 and then placing the cassette 22 in the recess 30 formed in the support tray 20. The user may then press start buttons 14 on the keyboard 12 to cause the controller 100 to retract the support tray 20 inwardly so that the window 28 in the reagent cassette 22 is illuminated by the light source 108 and so that one or more reflectance signals are generated by the detection apparatus. After the reflectance signals are generated and processed by the controller, the test results may be displayed on the display 16 and/or printed out by a printer 11.

In order to then perform one or more optical inspection tests on a reagent strip 46, the user would remove the reagent cassette 22 from the recess 30 in the support tray, discard the cassette 22, and place the reagent strip holder 40 in the recess 30 in the support tray 20.

To prepare a reagent strip 46 for optical inspection, the user would dip the reagent strip 46 into a body fluid sample to be tested so that the reagent pads 50 are immersed in the sample or otherwise apply the sample to the pads 50. After the side of the reagent strip 46 is blotted to remove excess fluid, the user places the strip 46 in the central channel 43 of the holder 40 and presses the start key 14 to initiate optical inspection of the reagent strip 46. The reagent strip holder 40 is then automatically retracted into the housing 17 and may be successively positioned at multiple locations within the inspection apparatus 10 so that each of the reagent pads 50 is optically inspected at an inspection location.

The provision of a support tray 20 which is adapted to be used with different types of liquid carriers allows the user to quickly and conveniently change the liquid carrier while allowing the inspection apparatus to optically inspect different types of liquid-carrying mechanisms. It should be noted that the support tray 20 does not have to be removed from the inspection apparatus 10 in order to replace one type of liquid carrier with another type of liquid carrier.

The tray assembly 200 of the present disclosure as shown in FIGS. 2 through 6 is an improvement over the tray assembly 20 shown in FIGS. 11 through 13 and can be used with the inspection apparatus 10 of FIG. 11 in a similar fashion as the tray assembly 20 of FIGS. 11 through 13. The inspection apparatus 100 of FIG. 1 is also an improvement over the inspection apparatus 10 of FIG. 11, and is similar in operation to the inspection apparatus 10 of FIG. 11. The improved inspection apparatus 100 of FIG. 1 is described in greater detail in PCT International Patent Application No. PCT/US2004/017339, filed Jun. 3, 2004 (International Publication No. WO 2005/001453, which is incorporated herein by reference. Components of the inspection apparatus 100 of FIG. 1 that are similar to the inspection apparatus 10 of FIG. 11 have the same reference numeral preceded by a "1". The inspection apparatus 100 of FIG. 1, however, includes a touch-screen display 115 in place of the keyboard 12 and the display screen 16 of FIG. 11. The inspection apparatus 100 of FIG. 1 also includes a door 119 in the opening 118, that opens upon the tray assembly 200 being extended out of the opening 118.

Figure 2:
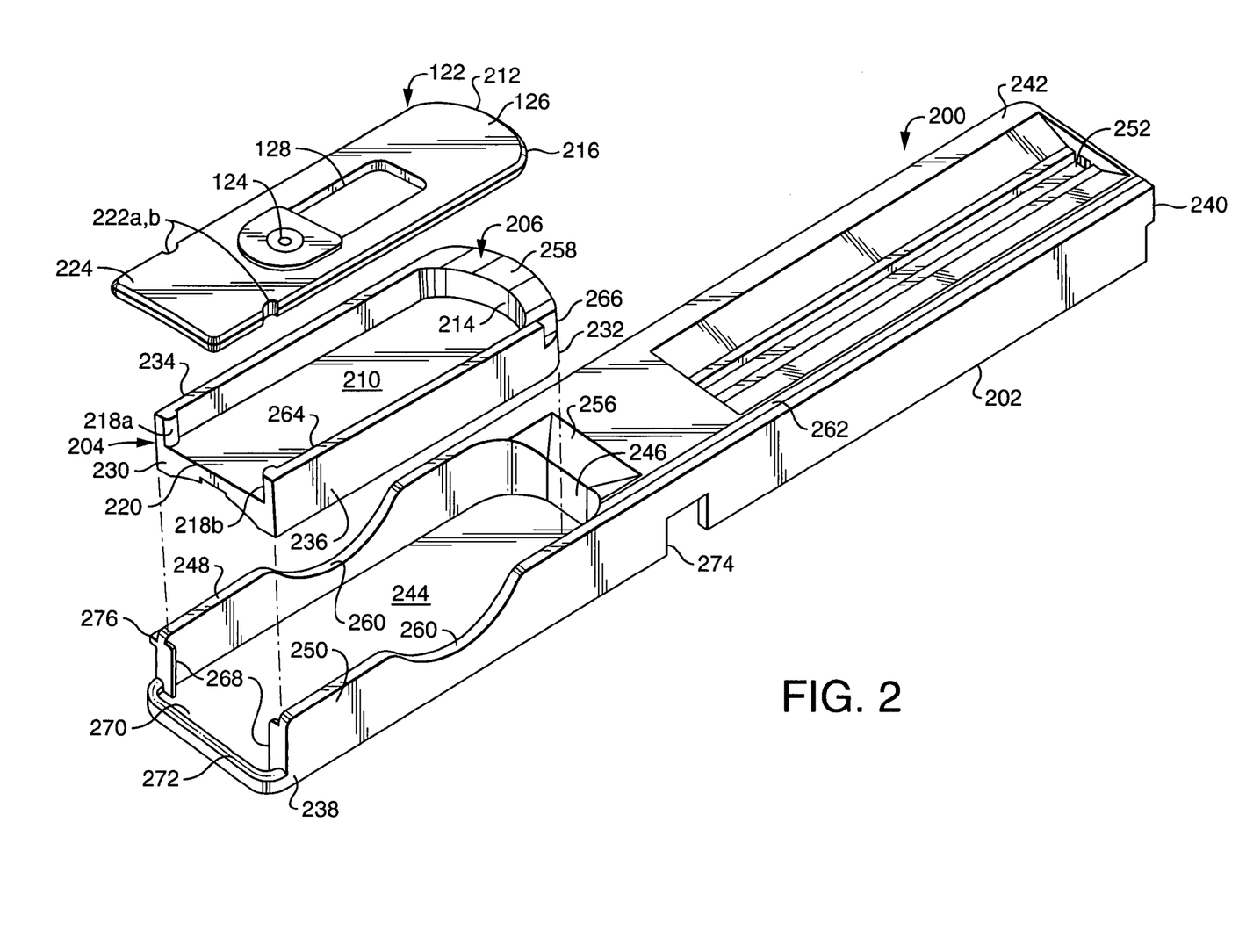
FIG. 2 is an end perspective view of an exemplary embodiment of a tray assembly constructed in accordance with the present disclosure for use with the apparatus of FIG. 1, wherein the assembly includes a support tray and an insert, and wherein the insert is shown being positioned in the support tray with a first surface facing upwardly so that a reagent cassette may be held by the insert in the support tray.
Figure 3:
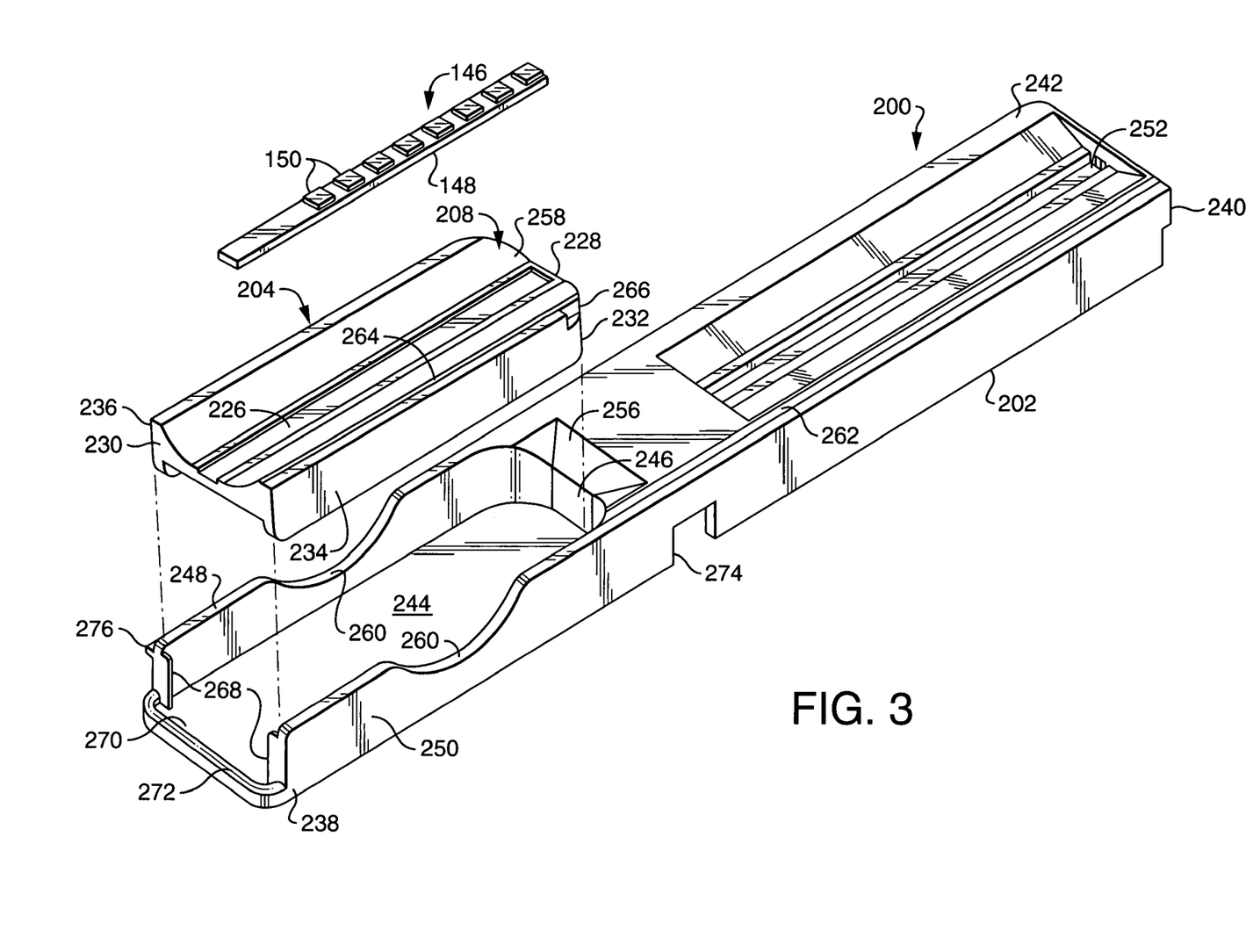
FIG. 3 is an end perspective view of the assembly of FIG. 2, wherein the insert is shown being positioned in the support tray with a second surface facing upwardly so that a reagent strip may be held by the insert in the support tray.

During use, the insert 204 of the tray assembly 200 of the present disclosure is removable from the support tray 202 and can be turned over and re-inserted into the support tray 202 depending upon which of the reagent cassette 122 and the reagent strip 146 is to be used with the tray assembly 200. The reagent cassettes 122 of FIG. 2 is similar to the reagent cassette 22 of FIG. 12 such that similar elements have the same reference numeral precede by a "1". In addition, the reagent strip 146 of FIG. 3 is similar to the reagent cassette 46 of FIG. 14 such that similar elements have the same reference numeral precede by a "1". Since the reagent cassette 122 and the reagent strip 146 do not directly touch the support tray 202, but are instead supported by the insert 204, the support tray 202 is less likely to be contaminated by excess bodily fluids from the reagent cassette 122 and the reagent strip 146. Instead, the insert 204 can be removed from the support tray 202 and cleaned of excess bodily fluids if necessary. In addition, the support tray 202 can also be easily cleaned upon removal of the insert 204.

Referring to FIG. 2, the first surface 206 of the insert 204 has a recess 210 shaped to receive a first portion 212 of the reagent cassette 122. An end wall 214 of the recess 210 of the first surface 206 of the insert 204 is curved to match a curved end wall 216 of the first portion 212 of the reagent cassette 122, to ensure that a user correctly orients the reagent cassette 122 within the insert 204. The insert 204 includes bosses 218a, 218b at an open end 220 of the recess 210 that are received in, respectively, indents 222a, 222b in the reagent cassette 122 to prevent the reagent cassette 122 from sliding out of the insert 204. Alternatively, the bosses can be provided on the reagent cassette 122 and the indents in the insert 204. A second portion 224 of the reagent cassette 122 extends outwardly beyond the open end 220 of the recess 210 when the reagent cassette 122 is correctly positioned within the insert 204. The second portion 224 of the reagent cassette 122 is separated from the first portion 212 of the reagent cassette 122 by the indents 222a, 222b of the reagent cassette 122. As is noticeable in FIG. 2, the second portion 224 of the reagent cassette 122 is shorter than the first portion 212 of the reagent cassette 122 to further ensure that a user correctly orients the reagent cassette 122 within the insert 204. In addition, the bosses 218a, 218b of the recess 210 are provided in slightly different sizes or shapes, and the indents 222a, 222b of the reagent cassette 122 are also provided in slightly different sizes or shapes, which match the bosses 218a, 218b, to prevent the reagent cassette 122 from being inserted into the insert 204 upside down.

Referring to FIG. 3, the second surface 208 of the insert 204 has an elongated channel 226 sized to accommodate the reagent strip 146. The second surface 208 of the insert 204 also has an end wall 228 closing the elongated channel 226 at an end of the insert 204, and a top surface of the end wall 228 is white (or other suitable color) such that the inspection apparatus 100 of FIG. 1 can use the white end wall 228 to determine if the reagent strip 146 is correctly abutting the end wall 228 during an inspection procedure.

As shown in FIGS. 2 through 4 and 6, the first and the second surfaces 206, 208 of the insert 204 face in opposite directions and the insert 204 also includes first and second opposing ends 230, 232 connecting the first and the second surfaces 206, 208, and first and second opposing sides 234, 236 connecting the first and the second surfaces 206, 208 and extending between the opposing ends 230, 232.

As shown in FIGS. 2 through 5, the support tray 202 includes first and second opposing ends 238, 240, a top surface 242 extending between the first and second opposing ends 238, 240 and having a compartment 244 extending from the first end 238 for receiving the insert 204. The compartment 244 includes an end wall 246 conforming to the second end 232 of the insert 204 and opposing first and second side walls 248, 250 extending from the end wall 246 and conforming to the first and second opposing sides 234, 236 of the insert 204.

The first and the second opposing ends 230, 232 of the insert 204 have different shapes to ensure that a user will correctly orient the insert 204 within the support tray 202 during use. In the exemplary embodiment of FIGS. 2 through 4 and 6, the shape of the first end 230 of the insert 204 is rectangular and the shape of the second end 232 of the insert 204 is curved.

Figure 4:
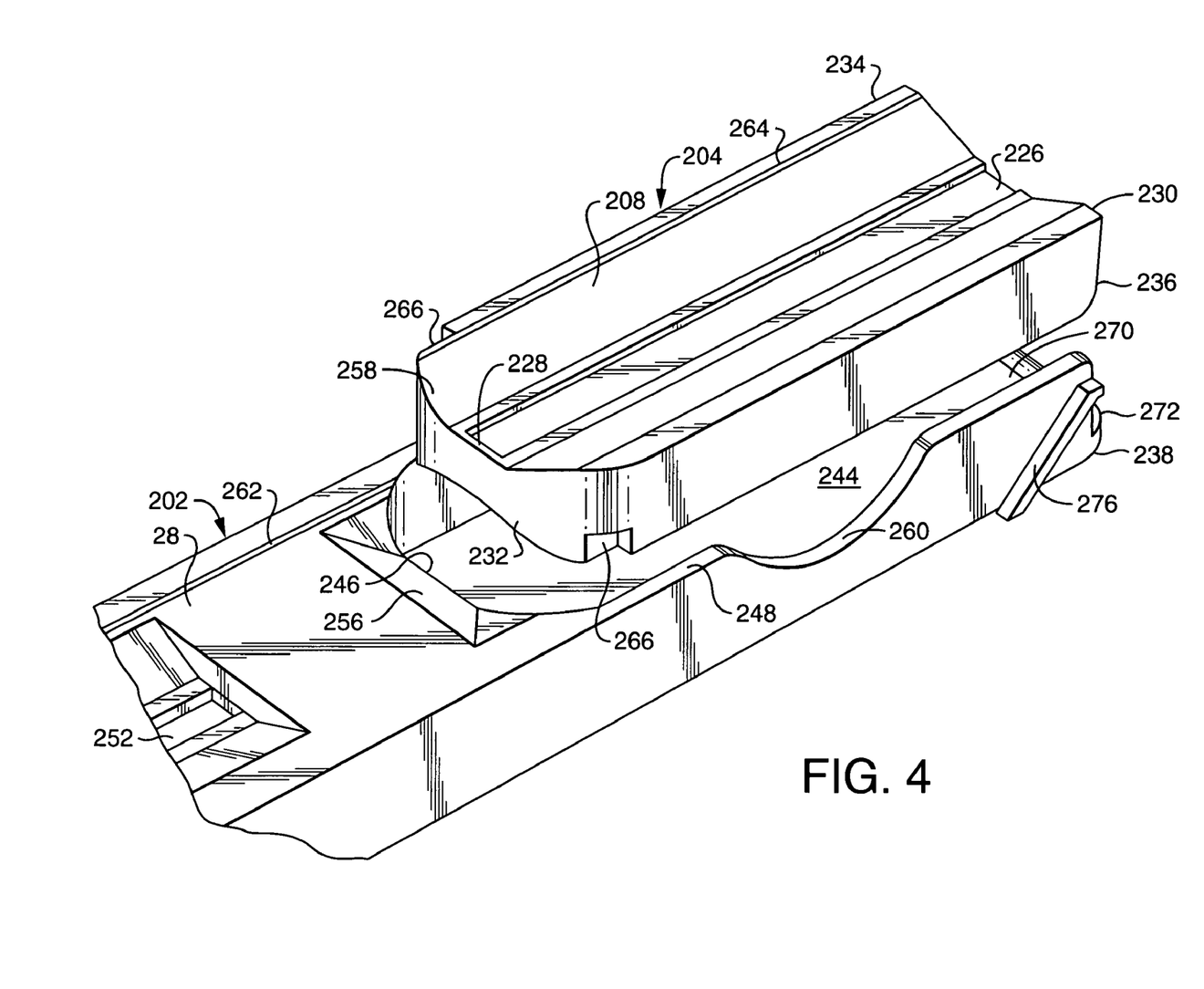
FIG. 4 is an enlarged, opposite end perspective view of a portion of the assembly of FIG. 2, wherein the insert is shown being positioned in the support tray with the second surface facing upwardly.

Referring to FIGS. 2 through 4, the top surface 242 of the support tray 202 includes an elongated channel 252 extending from the second end 240 of the support tray 202, and a white calibration strip (not shown) is received in the elongated channel 252 of the support tray 202. The top surface 242 of the support tray 202 also includes a sloped surface 256 extending from a center of the end wall 246 of the compartment 244, and the first and the second surfaces 206, 208 of the insert 204 include valleys or depressions 258 that correspond to the sloped surface 256 of the support tray 202 when the insert 204 is positioned within the compartment 244. The sloped surface 256 aids in the proper optical machine inspection of the reagent cassette 122 and the reagent strip 146.

In the exemplary embodiment show in FIGS. 2 through 5, the side walls 248, 250 of the compartment 244 of the support tray 202 include cut-outs 260 for allowing the sides 234, 236 of the insert 204 to be grasped when the insert 204 is positioned within the compartment 244. The support tray 202 also includes an elongated guide 262 extending from the compartment 244, and the first and the second surfaces 206, 208 of the insert 204, as shown in FIGS. 2 through 4 and 6, include elongated guides 264 that correspond to the elongated guide 262 of the support tray 202 when the insert 204 is positioned within the compartment 244. The guides comprise grooves 262, 264 that receive a wheel (not shown) mounted within the apparatus 100 of FIG. 1 that helps to smoothly guide and extend and retract the tray assembly 200 from the apparatus 100. The insert 204 also defines sinks 266 in the elongated guides 264 of the first and the second surfaces 206, 208, that prevent excess body fluids from flowing from the insert 204 and down the guide 262 of the support tray 202 (and thus into the apparatus 100). The sinks 266, therefore, help to prevent contamination of the apparatus 100 by excess bodily fluids contained on the insert 204 or the reagent cassette 122 or reagent strip 146.

Figure 5:
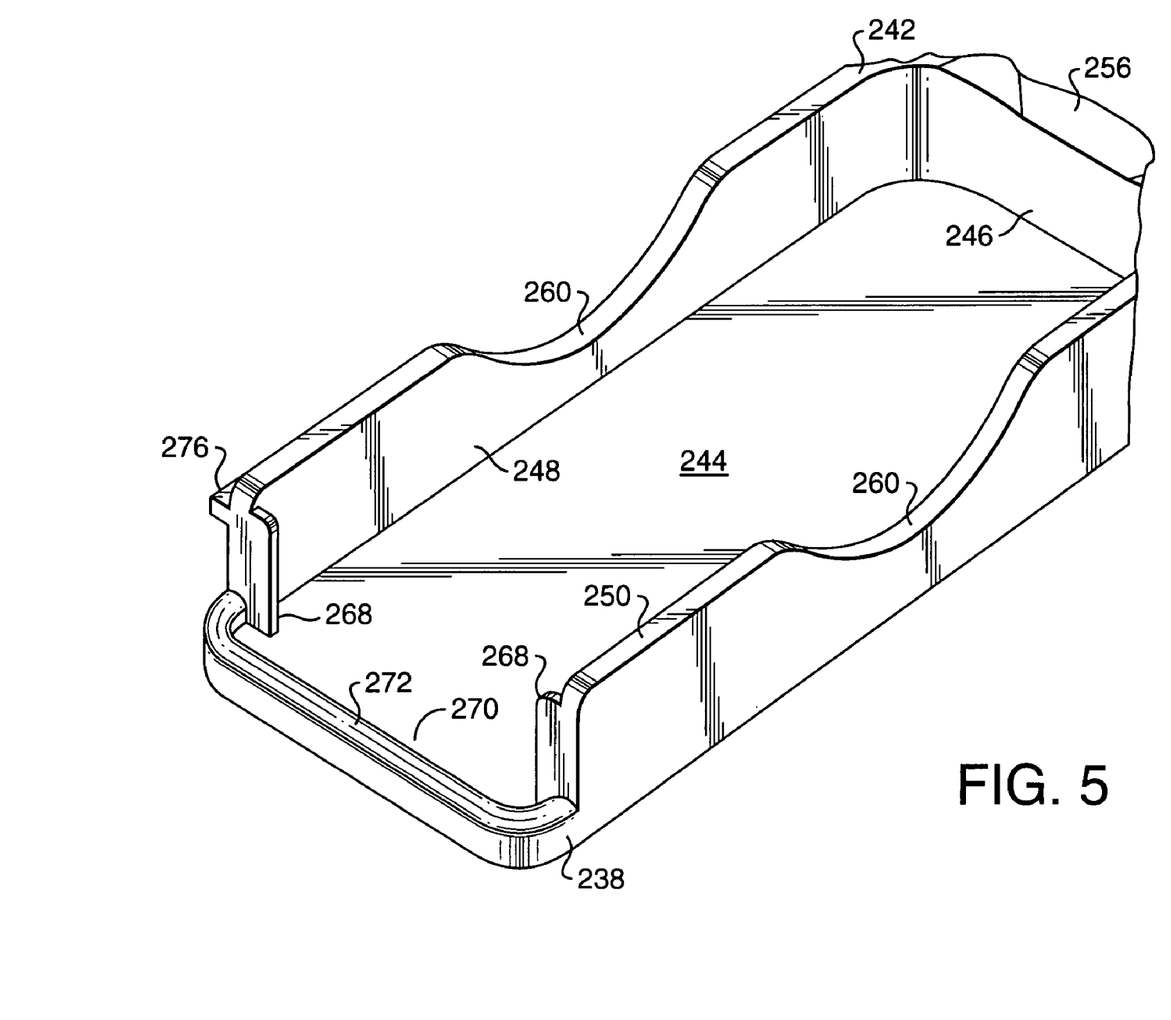
FIG. 5 is an enlarged, end perspective view of a portion of the support tray of the assembly of FIG. 2.
Figure 6:
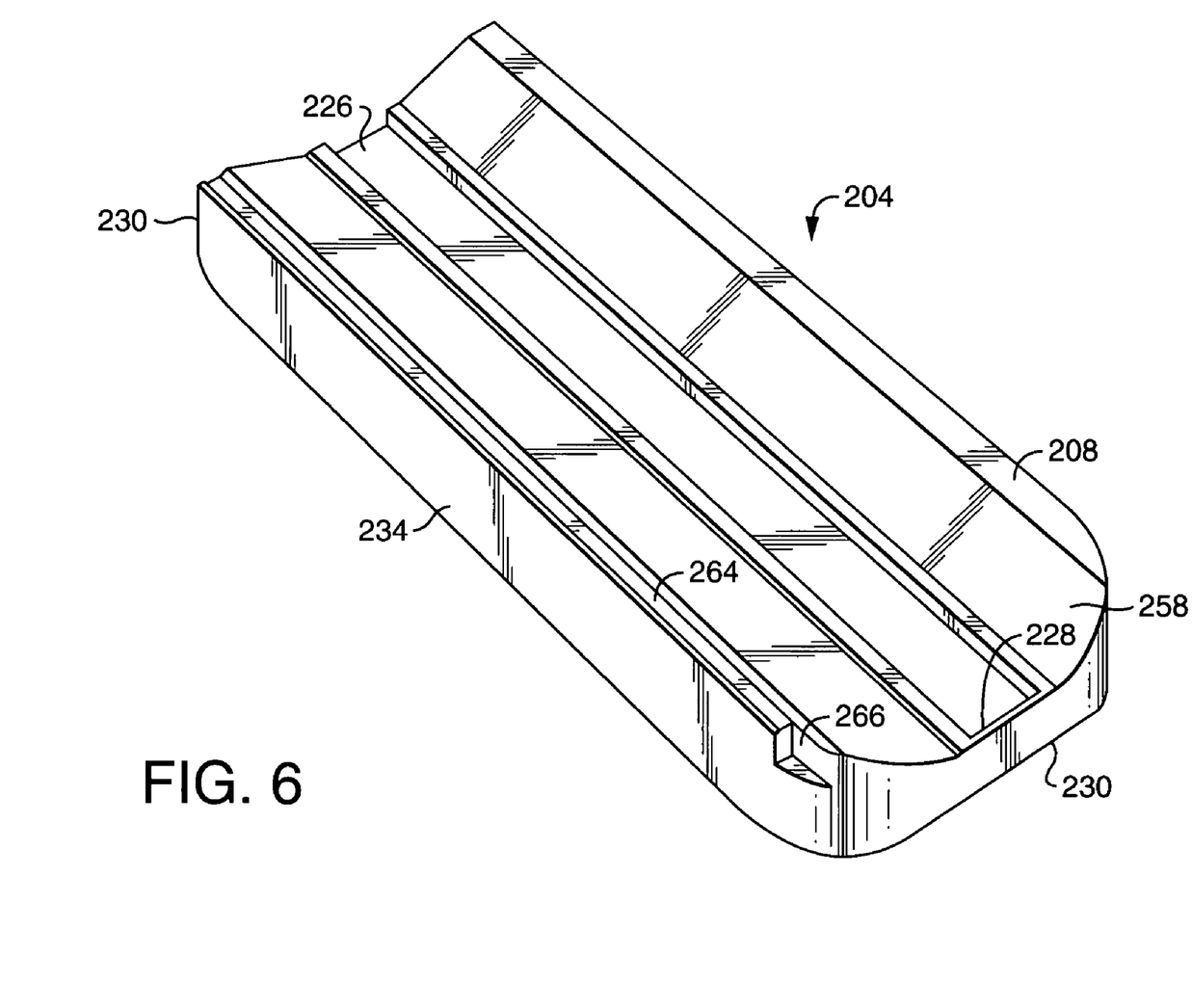
FIG. 6 is an enlarged, opposite end perspective view of the insert of the assembly of FIG. 2, wherein the second surface of the insert is shown facing upwardly.

As shown best in FIGS. 2, 3 and 5, the compartment 244 includes stops 268 for engaging the insert 204 when the insert 204 is positioned within the compartment 244, to prevent the insert 204 from sliding out of the compartment 244. In the exemplary embodiment shown, the stops 268 are positioned so that they engage the first end 230 of the insert 204 when the insert 204 is positioned within the compartment 244. The support tray 202 also includes a land 270 extending from the first end 238 and having a lip 272 for catching and containing excess fluid leaking from the insert 204 when the insert 204 is positioned in the compartment 244. The land 270 and the lip 272, therefore, also help to prevent contamination of the apparatus 100 by excess bodily fluids contained on the insert 204 or the reagent cassette 122 or reagent strip 146.

As shown in FIGS. 2 and 3, a notch 274 is provided in the side wall 250 of the support tray 202. The notch 274 is used for detection by another detector of the liquid sample inspection apparatus 100 of FIG. 1 when the support tray 202 is inserted into the apparatus 100.

As shown best in FIG. 4, the support tray 202 further includes a cam surface 276. The cam surface 276 is used to open the door 119 of the liquid sample inspection apparatus 100 of FIG. 1 when the support tray 202 is extended out from the apparatus 100, and causes the door 119 to close when the support tray 202 is retracted into the apparatus 100. Closing the door 119 during the detection phase prevents ambient light from entering into the apparatus 100 and causing an untoward result. In the exemplary embodiment of FIG. 4, the cam surface 276 extends from the first side wall 248 of the support tray 202.

Figure 7:
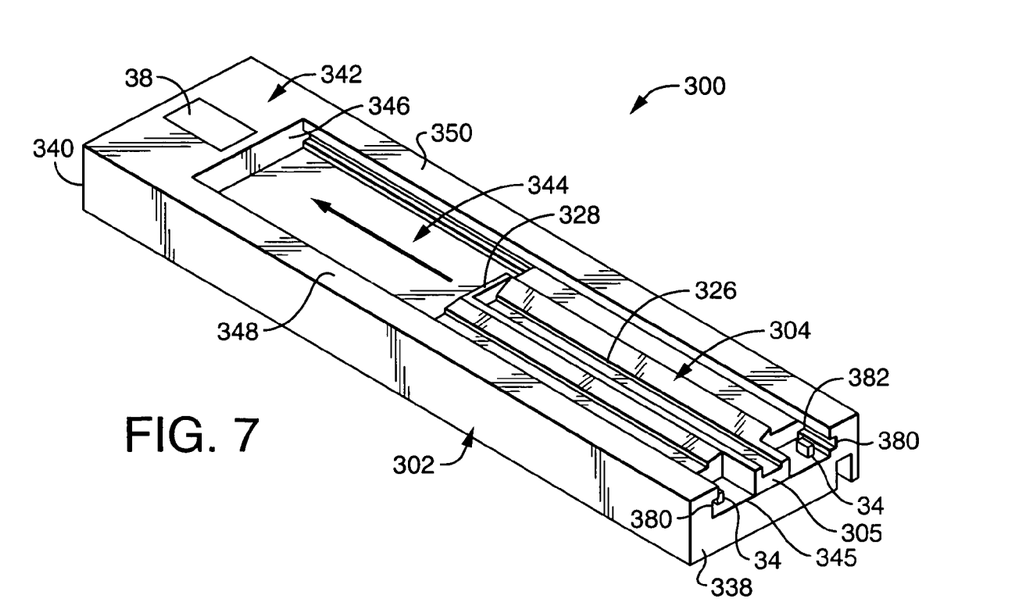
FIG. 7 is an end perspective view of another exemplary embodiment of a tray assembly constructed in accordance with the present disclosure for use with the apparatus of FIG. 1, wherein the assembly includes a support tray and an insert received for movement within the tray, and wherein the insert is shown in one position so that a reagent strip may be inserted into the insert in the support tray.
Figure 8:
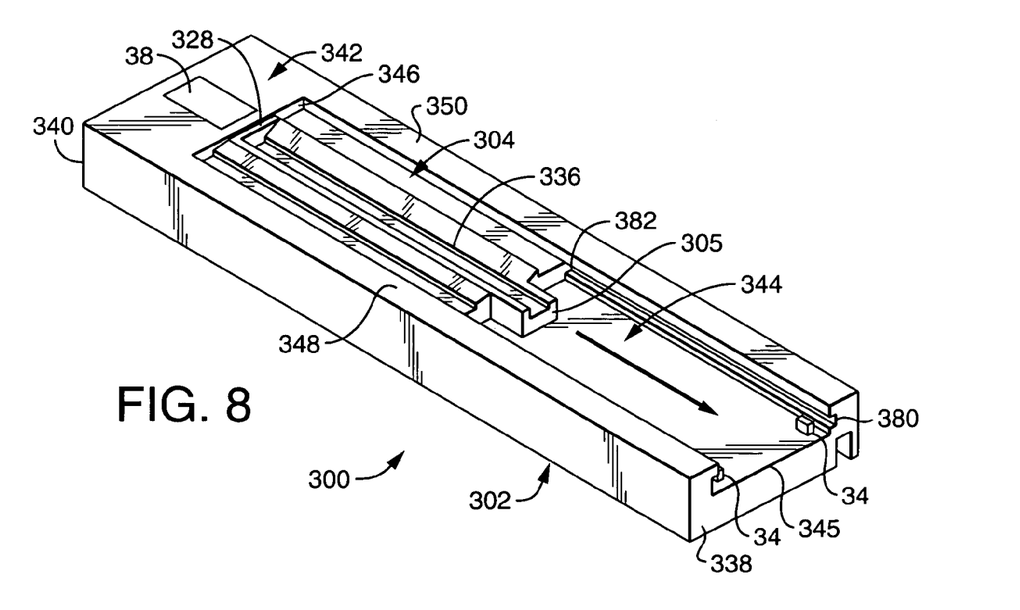
FIG. 8 is an end perspective view of the assembly of FIG. 7, wherein the insert is shown in another position allowing a reagent cassette to be inserted into the support tray.

FIGS. 7 and 8 show another exemplary embodiment of a tray assembly 300 constructed in accordance with the present disclosure for use with the apparatus 100 of FIG. 1. The assembly 300 includes a support tray 302 and an insert 304 received for movement within the tray. In FIG. 7 the insert 304 is shown in one position so that a reagent strip (not shown) may be inserted into the insert 304 and used with the tray assembly 300, while in FIG. 8 the insert 304 is shown in another position allowing a reagent cassette (not shown) to be inserted into the support tray 302. The insert 304 has the elongated channel 326 sized to accommodate the reagent strip, and an end wall 328 closing the channel 326 at an end of the insert 304.

The support tray 302 includes first and second opposing ends 338, 340 and a top surface 342 extending between the first and second opposing ends and having a compartment 344 extending from an open end 345 at the first end 338 of the support tray 302 to an end wall 346 nearer the second end 340 of the support tray 302. The insert 304 is movably supported within the compartment 344 of the support tray 302 and movable between a first position adjacent the end wall 346 of the compartment 344, as shown in FIG. 8, and a second position adjacent the open end 345 of the compartment 344, as shown in FIG. 7. A reagent cassette (not shown) is inserted into the compartment 344 between the open end 345 of the compartment and the insert 304 when the insert 304 is in the first position shown in FIG. 8. An end 305 of the insert 304 is abutted by the reagent cassette.

In the exemplary embodiment of FIGS. 7 and 8, the insert 304 is slidably movable within the compartment 344 of the support tray 302 between the first and the second positions. As shown, side walls 348, 350 of the compartment of the support tray 302 include channels 380 and sides of the insert 304 include rails 382 received in the channels 380 for guiding the sliding movement of the insert 304 within the compartment 344. The insert 304 is not removable from the support tray 302.

Figure 9:
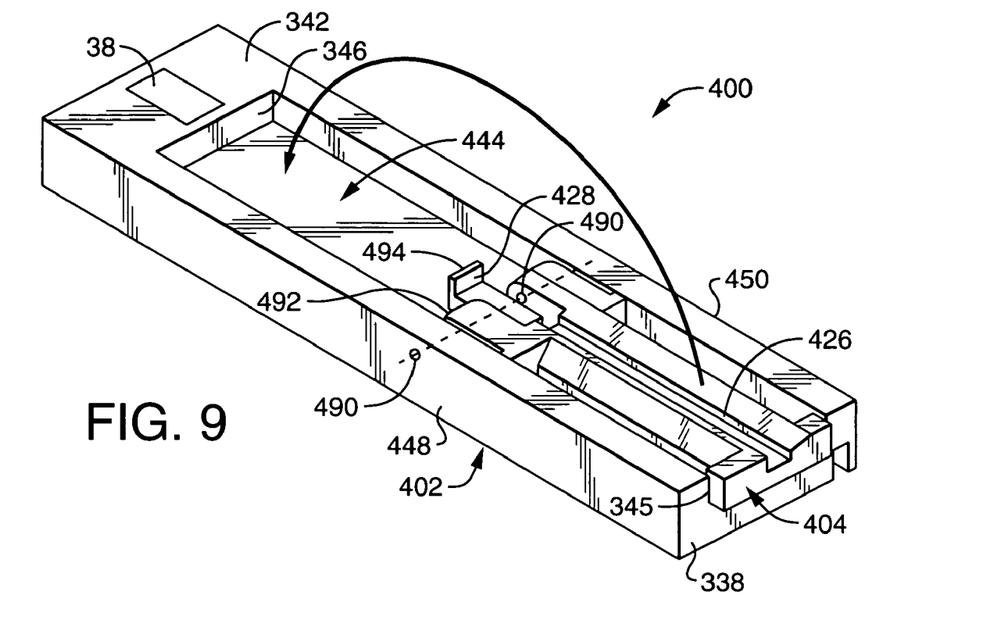
FIG. 9 is an end perspective view of an additional exemplary embodiment of a tray assembly constructed in accordance with the present disclosure for use with the apparatus of FIG. 1, wherein the assembly includes a support tray and an insert received for movement within the tray, and wherein the insert is shown in one position so that a reagent strip may be inserted into the insert in the support tray.
Figure 10:
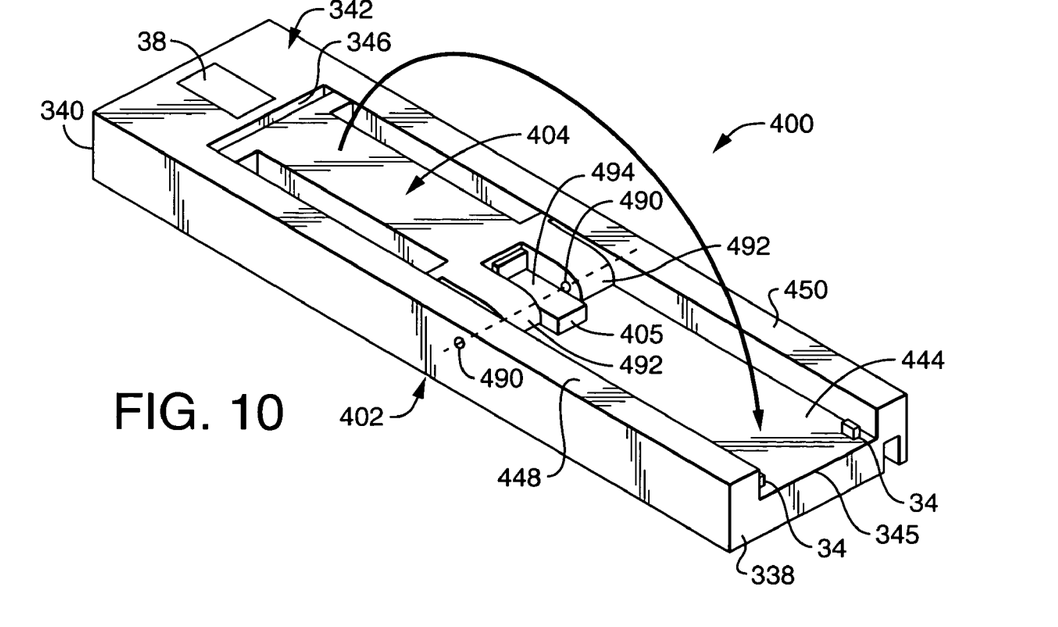
FIG. 10 is an end perspective view of the assembly of FIG. 9, wherein the insert is shown in another position allowing a reagent cassette to be inserted into the support tray.

A further exemplary embodiment of a tray assembly 400 constructed in accordance with the present disclosure for use with the apparatus 100 of FIG. 1 is shown in FIGS. 9 and 10. The assembly 400 is similar to the assembly 300 of FIGS. 7 and 8, but includes an insert 404 that is pivotally movable within a compartment 444 of a support tray 402 between a first position, shown in FIG. 10, and a second position, shown in FIG. 9. When the insert 404 is in the first position, the tray assembly 400 is adapted for receiving a reagent cassette (not shown) in the compartment 444 of the support tray 402. When the insert 404 is in the second position, the tray assembly 400 is adapted for receiving a reagent strip (not shown) in an elongated channel 426 in a surface of the insert 404.

The insert 404 is pivotally mounted to the support tray 402 by two pins 490 which extend through side walls 448, 450 of the support tray 402 and through hinges 492 of the insert 404. The insert 404 is not removable from the support tray 302. An anchor 494 is fixed to the floor of the compartment 444, between the hinges 492 of the insert 404, and provides an end wall 428 for the reagent strip to abut, and an end wall 405 for the reagent cassette to abut.

Numerous further modifications and alternative embodiments of the disclosure will be apparent to those skilled in the art in view of the foregoing description. This description is to be construed as illustrative only, and is for the purpose of teaching those skilled in the art the best mode of carrying out the disclosure. The details of the structure and method may be varied substantially without departing from the spirit of the disclosure, and the exclusive use of all modifications which come within the scope of the appended claims is reserved.

What is claimed is:

1. An assembly for use with an apparatus adapted to inspect a liquid sample, the tray assembly comprising:
   a support tray insertable within an inspection location within the liquid sample inspection apparatus so that a light source of the apparatus illuminates a liquid sample carried on the support tray and a detector of the apparatus receives light from the liquid sample when the support tray is positioned at the inspection location; and
   an insert supported within the support tray and having a first surface adapted to receive a first type of liquid carrier and a second surface adapted to receive a second type of liquid carrier different from the first type of liquid carrier,
   wherein the first type of liquid carrier comprises a reagent cassette and the first surface of the insert has a recess shaped to receive a first portion of the reagent cassette, and
   wherein one of a boss and an indent is disposed within the recess of the first surface of the insert, and the reagent cassette has the other of the boss and the indent, and wherein the indent receives the boss to correctly position the reagent cassette within the insert and prevent the reagent cassette from sliding out of the insert.

2. An assembly as defined in claim 1, wherein the boss is disposed within the recess of the first surface of the insert.

3. An assembly as defined in claim 1, wherein the insert is adapted such that a second portion of the reagent cassette will extend outwardly beyond a first end of the insert.

4. An assembly as defined in claim 1, wherein the second type of liquid carrier comprises a reagent strip having a plurality of reagent pads disposed thereon.

5. An assembly as defined in claim 4, wherein the second surface of the insert has an elongated channel sized to accommodate the reagent strip.

6. An assembly as defined in claim 5, wherein the second surface of the insert has an end wall closing the elongated channel at a second end of the insert, and wherein a top surface of the end wall is white.

7. An assembly as defined in claim 1, wherein:
the first and the second surfaces of the insert face in opposite directions and the insert also comprises:
first and second opposing ends connecting the first and the second surfaces; and
first and second opposing sides connecting the first and the second surfaces and extending between the opposing ends; and
the support tray includes a top surface having a compartment for receiving the insert and the compartment includes an end wall conforming to the second end of the insert and opposing first and second side walls extending from the end wall and conforming to the first and second opposing sides of the insert.

8. An assembly as defined in claim 7, wherein the first and the second opposing ends of the insert have different shapes.

9. An assembly as defined in claim 8, wherein the shape of the first end of the insert is rectangular and the shape of the second end of the insert is curved.

10. An assembly as defined in claim 1, wherein the support tray includes a top surface having a compartment for receiving the insert and the compartment includes an end wall, and the top surface of the support tray includes a sloped surface extending from a center of the end wall of the compartment, and the first and the second surfaces of the insert include depressions that correspond to the sloped surface of the support tray when the insert is positioned within the compartment.

11. An assembly as defined in claim 1, wherein the support tray includes a top surface having a compartment for receiving the insert and the compartment includes side walls, and the side walls include cut-outs for allowing the sides of the insert to be grasped when the insert is positioned within the compartment.

12. An assembly for use with an apparatus adapted to inspect a liquid sample, the tray assembly comprising:
a support tray insertable within an inspection location within the liquid sample inspection apparatus so that a light source of the apparatus illuminates a liquid sample carried on the support tray and a detector of the apparatus receives light from the liquid sample when the support tray is positioned at the inspection location; and
an insert supported within the support tray and having a first surface adapted to receive a first type of liquid carrier and a second surface adapted to receive a second type of liquid carrier different from the first type of liquid carrier,
wherein the support tray includes a top surface having a compartment for receiving the insert and an elongated guide extending from the compartment, and the first and the second surfaces of the insert include elongated guides that correspond to the elongated guide of the support tray when the insert is positioned within the compartment.

13. An assembly as defined in claim 12, wherein the elongated guides comprise grooves.

14. An assembly as defined in claim 12, wherein the insert defines sinks in the elongated guides of the first and the second surfaces.

15. An assembly as for use with an apparatus adapted to inspect a liquid sample, the tray assembly comprising:

a support tray insertable within an inspection location within the liquid sample inspection apparatus so that a light source of the apparatus illuminates a liquid sample carried on the support tray and a detector of the apparatus receives light from the liquid sample when the support tray is positioned at the inspection location; and
an insert supported within the support tray and having a first surface adapted to receive a first type of liquid carrier and a second surface adapted to receive a second type of liquid carrier different from the first type of liquid carrier,
wherein the support tray includes a top surface having a compartment for receiving the insert and the compartment includes stops for engaging the insert when the insert is positioned within the compartment, to prevent the insert from sliding out of the compartment.

16. An assembly as defined in claim 15, wherein the stops of the support tray engage a first end of the insert when the insert is positioned within the compartment.

17. An assembly as defined in claim 1, wherein the support tray includes first and second opposing ends, a top surface extending between the first and second opposing ends and having a compartment extending from the first end for receiving the insert, and wherein the top surface of the support tray includes an elongated channel extending from the second end of the support tray, and a calibration strip is received in the elongated channel of the support tray.

18. An assembly as defined in claim 1, wherein the support tray includes first and second opposing ends, a top surface extending between the first and second opposing ends and having a compartment extending from the first end for receiving the insert, and the support tray includes a land extending from the first end and having a lip for catching fluid leaking from the insert when the insert is positioned in the compartment.

19. An assembly as defined in claim 1, wherein the support tray includes a side wall having a notch for detection by another detector of the liquid sample inspection apparatus when the support tray is inserted into the apparatus.

20. An assembly for use with an apparatus adapted to inspect a liquid sample, the tray assembly comprising:
a support tray insertable within an inspection location within the liquid sample inspection apparatus so that a light source of the apparatus illuminates a liquid sample carried on the support tray and a detector of the apparatus receives light from the liquid sample when the support tray is positioned at the inspection location; and
an insert supported within the support tray and having a first surface adapted to receive a first type of liquid carrier and a second surface adapted to receive a second type of liquid carrier different from the first type of liquid carrier,
wherein the support tray includes a cam surface for opening a door of the liquid sample inspection apparatus when the support tray is extended from the apparatus and closing the door when the support tray is retracted into the apparatus.

21. An assembly as defined in claim 20, wherein the support tray includes a side wall and the cam surface extends from the side wall.

22. A system including the tray assembly of claim 20, and further including a liquid sample inspection apparatus comprising:
an opening into which the tray assembly is retracted and extended;

an inspection location within the opening for receiving the tray assembly;

a door which opens and closes the opening;

a light source for illuminating a liquid sample carried on the tray assembly when the support tray is received in the inspection location; and a detector for receiving light reflected off the liquid sample from the light source;

wherein the cam surface of the support tray of the tray assembly interacts with the door of the inspection apparatus such that the cam surface opens the door when the support tray is extended from the apparatus and allows the door to close when the support tray is retracted into the apparatus.

23. An assembly for use with an apparatus adapted to inspect a liquid sample, the tray assembly comprising:

a support tray insertable within an inspection location within the liquid sample inspection apparatus so that a light source of the apparatus illuminates a liquid sample carried on the support tray and a detector of the apparatus receives light from the liquid sample when the support tray is positioned at the inspection location; and an insert supported within the support tray and having a first surface adapted to receive a first type of liquid carrier and a second surface adapted to receive a second type of liquid carrier different from the first type of liquid carrier, wherein the first and the second surfaces of the insert include elongated guides.

24. An assembly as defined in claim 23, wherein the elongated guides comprise grooves.

25. An assembly as defined in claim 24, wherein the insert defines sinks in the elongated guides of the first and the second surfaces.

26. A system including the tray assembly of claim 1, and further including a liquid sample inspection apparatus comprising:

an inspection location for receiving the tray assembly;

a light source for illuminating a liquid sample carried on the tray assembly when the support tray is received in the inspection location; and a detector for receiving light reflected off the liquid sample from the light source.

* * * * *